Figure 1:
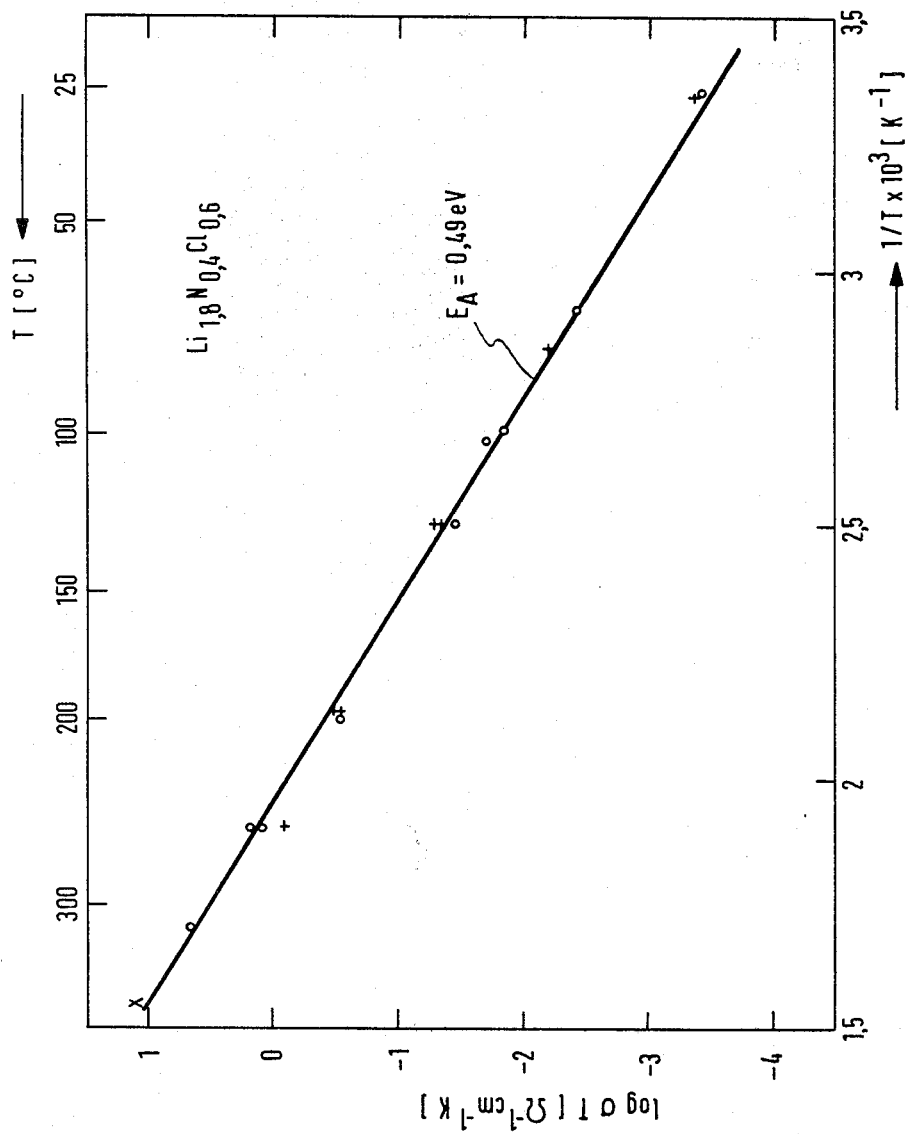

United States Patent [19]
Wichelhaus et al.

[11] 4,419,421
[45] Dec. 6, 1983

[54] ION CONDUCTOR MATERIAL

[75] Inventors: Winfried Wichelhaus, Ingelheim am Rhein; Werner Weppner, Stuttgart; Peter Hartwig, Weinheim, all of Fed. Rep. of Germany

[73] Assignee: Max-Planck-Gesellschaft zur Förderung der Wissenschaften E.V., Gottingen, Fed. Rep. of Germany

[21] Appl. No.: 313,870

[22] Filed: Oct. 22, 1981

Related U.S. Application Data

[63] Continuation of Ser. No. 110,584, Jan. 9, 1980.

[30] Foreign Application Priority Data

Jan. 15, 1979 [DE] Fed. Rep. of Germany ....... 2901303

[51] Int. Cl.³ ............................................. H01M 6/18
[52] U.S. Cl. .................................. 429/191; 429/199; 423/472
[58] Field of Search ................. 429/191, 193, 199, 30, 429/33; 252/62.2; 361/433; 204/195 S; 423/351, 472

[56] References Cited

U.S. PATENT DOCUMENTS 4,007,122 2/1977 Owens et al. .................... 429/193 X

*Primary Examiner*—Anthony Skapars
*Attorney, Agent, or Firm*—Felfe & Lynch

[57] ABSTRACT

The present invention provides compounds of the general formula:

$$Li_{2-2x}N_{0.5-x}Hal_{0.5+x}$$

wherein Hal is bromine, chlorine, fluorine or iodine and x is 0 or a number of up to 0.2 but excluding $Li_9N_2Cl_3$ and $Li_5NI_2$.

The present invention also provides solid ion conductor material, consisting of a compound of the general formula:

$$Li_{2-2x}N_{0.5-x}Hal_{0.5+x}$$

wherein Hal is bromine, chlorine, fluorine or iodine and x is 0 or a number of up to 0.2

Furthermore, the present invention provides processes for the production of these compounds and solid ion conductor materials, as well as galvanic cells comprising them.

5 Claims, 2 Drawing Figures

ION CONDUCTOR MATERIAL

This is a continuation of application Ser. No. 110,584, filed Jan. 9, 1980.

This invention relates to a solid ion conductor material and new compounds contained therein, and methods for their production. In additional aspect, the invention relates to the use of such solid ion conductor materials in galvanic cells, such as primary and secondary batteries, electrochromic displays, memory elements and timers.

Because of the low equivalent weight and of the strongly electropositive character of lithium, as well as the sufficient occurrence of lithium-containing raw materials, ion-conducting lithium compounds are preferred to other ion-conducting compounds for a technological utilization. Therefore, ion-conducting lithium compounds are sought which satisfy the following conditions as ideally as possible:

1. High ionic conductivity with comparatively low electron conductivity;
2. Thermodynamic stability towards lithium;
3. High thermodynamic decomposition voltage;
4. Thermodynamic stability towards electrode materials which are employed in galvanic cells;
5. Cost-favorable production of the electrolyte.

Ion-conducting lithium compounds are already known which possess crystal structures which are the same as or similar to those of the known $Na^+$ ion conductors, such as $Na\text{-}\beta\text{-}Al_2O_3$ and $Na_3Zr_2PSi_2O_{12}$, and are characterized by open structures for the $Li^+$ ions. Some of these compounds admittedly show a considerable ion conductivity but the possibilities of using them remain small since these electrolytes are not stable towards lithium, lithium alloys or metallic lithium phases with sufficient lithium activity for a use (see Superionic Conductors, pub. by G. D. Mahan and W. L. Roth, Plenum Press, New York and London, 1976).

Hitherto, only lithium nitride ($Li_3N$) has become known as the sole lithium compound with high ion conductivity and thermodynamic stability towards lithium. Lithium nitride is characterized by an ordered crystal lattice which only displays a small number of lithium defects. The high ion conductivity is limited to two spatial directions of the crystal. Contaminations by foreign atoms have proved to be especially disadvantageous for the $Li^+$ ion conduction, these contaminations getting into the lithium nitride when commercially available lithium is employed for the production thereof. A further disadvantage of lithium nitride is its low thermodynamic decomposition voltage of 0.44 V. Admittedly, energy cells with a cell voltage of above 0.44 V can be constructed on the basis of a kinetic inhibition or passivation of the electrolyte surface but this is unsuitable for use at comparatively high temperatures and for long periods of operation.

Lithium compounds with perfect anti-$CaF_2$ structure display only low ion conductivities: $\sigma_{ionic}$ of $Li_2O$ and $Li_2S$ smaller than $10^{-8}\Omega^{-1}cm^{-1}$ at ambient temperature.

Therefore, it is an object of the present invention to find or to provide ion-conducting lithium compounds which better fulfill the above-stated five conditions for ideal ion conductors than the previously known ion conductors based on lithium, especially high thermodynamic stability towards lithium, high thermodynamic decomposition voltage and high thermodynamic stability towards electrode materials, are less sensitive towards contaminations and the ion conductivity of which is not limited to two spatial directions of the crystal.

Thus, according to the present invention, there is provided a solid ion conductor material which consists of a compound of the general formula:

$$Li_{2-2x}N_{0.5-x}Hal_{0.5+x}$$

wherein Hal is bromine, chlorine, fluorine or iodine and x is 0 or a number up to 0.2.

The ion conductor material according to the present invention preferably exists in the form of crystals which display a defective anti-$CaF_2$ structure.

Most of the compounds of which the ion conductor material according to the present invention consists are new. Therefore, the present invention also provides compounds of the general formula:

$$Li_{2-2x}N_{0.5-x}Hal_{0.5+x}$$

wherein Hal is bromine, chlorine, fluorine or iodine and x is 0 or a number up to 0.2, but excluding $Li_9N_2Cl_3$ and $Li_5NI_2$.

The solid ion conductor material according to the present invention (also referred to as solid electrolyte) displays a high ion conductivity and, in contradistinction to known lithium compounds with similar electrolytic properties, also possesses a high thermodynamic stability. Furthermore, it is simple to obtain.

From Z. anorg. allg. Chem. 379, 293/1970, there is already known the compound $Li_9N_2Cl_3$, its production and its crystal structure. This compound is one of the two phases which, in the ternary system lithium-nitrogen-chlorine, besides the binary lithium compounds $Li_3N$ and $LiCl$, were known and which lie on the quasi binary cut between $Li_3N$ and $LiCl$. The physical properties, especially the ion and electron conductivity, were hitherto not known. In the same way, there was no indication that this compound could be useful as a solid electrolyte.

As halide, in the scope of the present invention, the chloride is preferred. The present invention also includes mixtures of the said halides, i.e. compounds in which Hal consists of two, three or four of the mentioned halides.

The present invention also provides a process for the production of the compounds according to the present invention or of the ion conductor material according to the present invention, wherein either (a) lithium nitride and lithium halide are intimately mixed in the desired combination of appropriate molar proportions, under inert gas, the mixture is pressed at a pressure of at least 20 MPa, the pressed bodies obtained are rapidly heated in an atmosphere of nitrogen to 460° to 550° C. and thereafter heat treated at 350° to 450° C. until the reaction is ended, or (b) lithium halide and lithium metal are mixed in the desired molar ratio and heated under nitrogen until the nitrogen pressure remains constant.

According to the present invention, there can also be used a mixture of various lithium halides selected from lithium fluoride, lithium chloride, lithium bromide and lithium iodide.

The pressure employed for pressing the mixture of lithium nitride and lithium halide can be any one which is technically feasible and is above the given lower boundary value, pressing preferably being carried out at a pressure of from about 90 to about 120 MPa.

The pressed bodies so produced are subsequently rapidly heated to a temperature which lies somewhat above the intended heat treating temperature. "Rapidly" is hereby to be understood to mean a period of time of from about 2 to about 15 minutes and preferably of from about 3 to about 8 minutes. Heating is preferably carried out at a temperature of from 480° to 520° C.

The period and temperature of the subsequent heat treatment depends upon the applied pressure. If the nitrogen pressure corresponds to atmospheric pressure, i.e. no increased pressure is applied, then the reaction normally takes about 2 to 25 hours and preferably 15 to 25 hours when maintaining a temperature of from 425° to 445° C. The end of the reaction can be ascertained when the reaction product is found to be phase pure by X-rays. The period of the temperature treatment to be applied for this purpose in the case of the various temperatures which can be employed can easily be ascertained by preliminary experiments.

In the case of increased pressure, the period and/or temperature of the heat treatment can be reduced. In general, therefore, the reaction can be carried out at increased pressures within a period of time of from 5 to 120 minutes, temperatures of from about 200° to 430° C. thereby being employed. This embodiment of the process according to the present invention can be carried out, for example, in a pressure sinter press (hot press).

This variant of the process according to the present invention can be carried out with pressed bodies of any desired shape, for example, with tablets, crucibles, tubes, plates and the like.

The second variant of the process according to the present invention, in which a mixture of metallic lithium and lithium halide is heated with nitrogen, can be carried out at temperatures in the range of from about 150° to 500° C., a range of 180° to 230° C. being preferred. The nitrogen partial pressure should be from 1 to 100 kPa. The nitrogen can be used in pure form or in a mixture with other inert gases. The end of the reaction can be recognized when no further nitrogen is taken up, i.e. the nitrogen pressure remains constant.

Although it is a characteristic of the process according to the present invention that specially pure starting materials do not have to be employed, nevertheless, unnecessary impurities are preferably avoided. Therefore, the process according to the present invention is also preferably carried out in a vessel made of a material which is not attacked by lithium metal, for example molybdenum, tungsten or stainless steel. However, as already mentioned, impurities, for example lithium oxide, do not reduce the conductivity of the electrolytes according to the present invention since they are taken up by lithium nitride halide with mixed crystal formation.

The lithium nitride halides produced by the process according to the present invention, crystallizing in the anti-CaF$_2$ type, are, depending upon their composition, characterized by differing proportions of Li$^+$ defects. According to the findings on other ion conductors, it is to be assumed that these lattice defects are important for the ascertained high ion conductivity. Thus, for example, in Li$_{1.8}$N$_{0.4}$Cl$_{0.6}$, about 10% of the lattice sites for Li$^+$ are unoccupied. On ion conductors according to the present invention of this composition in tablet form, there were measured the conductivities in the temperature range of 25° to 400° C. The results obtained are shown in FIG. 1 of the accompanying drawings. Ion conductivity $\sigma$ in $\Omega^{-1}$ cm$^{-1}$ at 25° C. was found to be $1.4 \times 10^{-6}$ and at 250° C. to be $2.4 \times 10^{-3}$. The electron conductivity is, in the whole of this temperature range, smaller by more than the factor of $10^4$. The activation enthalpy for $\sigma_{ionic}$ T was 0.49 eV. A linear dependence was ascertained between log $\sigma$ and the inverse temperature (1/T). The thermodynamic decomposition voltage in inert gas is greater than 2.5 V. In the case of higher nitrogen and halogen partial pressures, the decomposition takes place at higher voltages.

The ion conductor produced by the process according to the present invention is also characterized by a high phase purity. Only at the points of contact with the material of the apparatus in which the temperature treatment is carried out slight surface reactions occur which can easily be removed and exert no influence upon the conductivity properties. The electrolytes according to the present invention are stable towards solid and molten lithium.

The solid ion conductor material according to the present invention is especially useful as an electrolyte in galvanic cells, for example, in primary or secondary batteries, electrochromic indicators (display systems), timers and memory elements. Therefore, the present invention also provides a galvanic cell which comprises at least one ion conductor material arranged between electrodes, the ion conductor materials being a compound of the general formula:

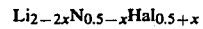

$$Li_{2-2x}N_{0.5-x}Hal_{0.5+x}$$

wherein Hal is bromine, chlorine, fluorine or iodine and x is 0 or a number of up to 0.2. A galvanic cell of this type has at least one lithium source electrode, for example metallic lithium or lithium alloy, as well as at least one further positive electrode which can be, for example, titanium or molybdenum sulphide.

The following Examples are given for the purpose of illustrating the present invention:

EXAMPLE 1

40 Mol % Li$_3$N and 60 mol % LiCl were intimately mixed under an inert gas to give a mixture of the sum composition Li$_{1.8}$N$_{0.4}$Cl$_{0.6}$. The mixture was pressed at a pressure of 100 MPa (corresponding to 1000 Kp/cm$^2$) to give tablets of 10 mm. diameter and 2 to 5 mm. thickness. The tablets were placed in a molybdenum container and heated in an atmosphere of nitrogen. For this purpose, they were first heated quickly (within about 5 minutes) to 500° C. and thereafter heated for 20 hours at 435° C., while maintaining the nitrogen atmosphere. Thereafter, the samples were allowed to cool. After cooling, hard, sintered tablets were obtained which can be stored without change in dry air.

In analogous manner, there were also prepared the compounds Li$_{1.6}$N$_{0.3}$Cl$_{0.7}$ and Li$_6$NBr$_3$, the starting materials and the amounts employed being correspondingly changed.

EXAMPLE 2

Figure 2:
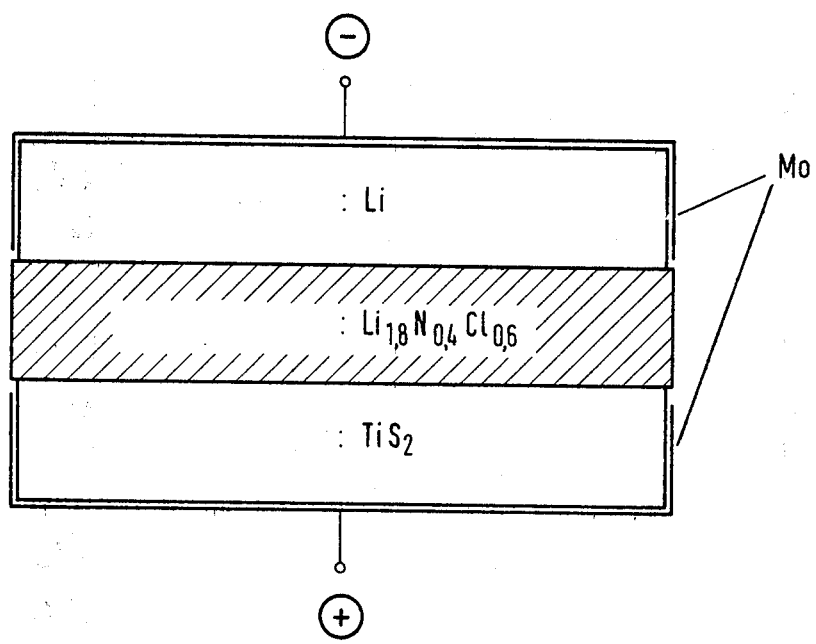

From a tablet of Li$_{1.8}$N$_{0.4}$Cl$_{0.6}$ produced according to Example 1 there was produced an energy cell by pressing lithium metal on one side and a TiS$_2$ tablet on the other side. The cell thus obtained was then contacted on both sides with molybdenum sheets to give the arrangement illustrated in FIG. 2 of the accompanying drawings.

The energy cell thus obtained gave a voltage of 2.9 V, which corresponds to the thermodynamically calculated value. The cell can be satisfactorily operated in the temperature range of from 25° to 130° C. and discharged via various resistances. The values thereby measured for the current strength corresponded to those which were determined on the basis of the conductivity measurements.

It will be understood that the specification and examples are illustrative, but not limitative of the present invention and that other embodiments within the spirit and scope of the invention will suggest themselves to those skilled in the art.

What is claimed is:

1. Solid ion conductor consisting of a compound selected from $Li_{1.8}N_{0.4}Cl_{0.6}$
$Li_{1.6}N_{0.3}Cl_{0.7}$
$Li_6NBr_3$.

2. Galvanic cell comprising at least one ion conductor material arranged between electrodes wherein the ion conductor material consists of a compound of the formula $Li_{2-2x}N_{0.5-x}Hal_{0.5+x}$ wherein
Hal is bromine, chlorine, fluorine or iodine
x is 0 or a number of up to 0.2.

3. Galvanic cell as claimed in claim 2 wherein one electrode is of lithium, metal or alloy and one electrode is of titanium or molybdenum sulfide.

4. A solid ion conductor cell comprising
first and second electrodes spaced apart from each other; and
an ion conductor material consisting of a compound of the formula $Li_{2-2x}N_{0.5-x}Hal_{0.5+x}$ wherein
Hal is bromine, chlorine, fluorine or iodine and
x is 0 or a number up to 0.2.

5. Method of conducting ions which comprises conducting said ions through a compound of the formula $Li_{2-2x}N_{0.5-x}Hal_{0.5+x}$ wherein
Hal is bromine, chlorine, fluorine or iodine and
x is 0 or a number up to 0.2.

* * * * *